United States Patent [19]

Cooper

[11] 4,390,473
[45] Jun. 28, 1983

[54] RECOVERY OF RHODIUM AND COBALT LOW PRESSURE OXO CATALYST

[75] Inventor: James L. Cooper, Longview, Tex.

[73] Assignee: Eastman Kodak Company, Rochester, N.Y.

[21] Appl. No.: 390,493

[22] Filed: Jun. 21, 1982

Related U.S. Application Data

[63] Continuation-in-part of Ser. No. 276,389, Jun. 22, 1981, abandoned.

[51] Int. Cl.$^3$ ............................................. C07F 15/00
[52] U.S. Cl. ................................. 260/429 R; 252/414; 252/416; 252/419; 260/439 R; 423/22; 423/139
[58] Field of Search .................. 423/22, 139; 252/414, 252/416, 419; 260/429 R, 439 R; 568/454

[56] References Cited

U.S. PATENT DOCUMENTS

| | | | |
|---|---|---|---|
| 3,298,779 | 1/1967 | Goto et al. | 423/139 |
| 3,901,822 | 8/1975 | Browning et al. | 252/416 |
| 3,904,547 | 9/1975 | Aycock et al. | 260/439 R |
| 4,021,463 | 5/1977 | Kummer et al. | 260/429 R |
| 4,164,481 | 8/1979 | Ma et al. | 252/414 |
| 4,196,096 | 4/1980 | Dawes et al. | 252/414 |
| 4,283,304 | 8/1981 | Bryant et al. | 260/429 R |

FOREIGN PATENT DOCUMENTS 879601  8/1971  Canada ................................. 423/22

*Primary Examiner*—Herbert T. Carter
*Attorney, Agent, or Firm*—Donald W. Spurrell; Daniel B. Reece, III

[57] ABSTRACT

Disclosed is a process for recovering rhodium and cobalt from a low pressure oxo catalyst solution containing ligandized (modified) rhodium and cobalt, organic solvent, and at least trace amounts of oxo aldehyde, which comprises contacting the catalyst solution with an oxygen containing gas and aqueous formic acid to form an organic phase and an aqueous phase, wherein the aqueous phase contains rhodium formate and cobalt formate solublized therein, and thereafter separating said phases to isolate said formates from the organic solvent, by-products and the like, for recycle to the reactor or for further treatment for use in the same or different processes.

7 Claims, No Drawings

RECOVERY OF RHODIUM AND COBALT LOW PRESSURE OXO CATALYST

DESCRIPTION

This is a continuation-in-part application of Ser. No. 276,389, filed June 22, 1981 and now abandoned.

This invention concerns the recovery of mixed ligandized (modified) rhodium and cobalt catalyst for subsequent use in either modified or unmodified form for low or high pressure oxo processes respectively.

In the present low pressure oxo processes, the active catalyst species typically comprises one or both of rhodium and cobalt in an active form such as their complexes with triphenylphosphine or the like, carbon monoxide and hydrogen, which complexes may be referred to as "modified" rhodium and cobalt, a specific apparent structure being e.g., $HRh(CO)(P\phi_3)_3$, rhodium hydridocarbonyl tristriphenylphosphine. Such catalyst periodically must be reactivated and/or recovered from the oxo by-products, e.g., from by-product purge streams, the cost of the catalyst otherwise being prohibitive.

Many rhodium catalyst recovery schemes have been developed and are disclosed in the patent literature, such as (1) contacting the catalyst stream with either steam or hydrogen under high temperatures and pressures; (2) precipitation of the metal onto a support; (3) adsorption of the rhodium catalyst onto ion exchange materials or such materials as magnesium silicate; (4) alloying the rhodium carbonyl catalysts with materials such as mercury; (5) decomposing unmodified rhodium carbonyl complexes by heating with aqueous formic acid which dissolves the rhodium into the aqueous phase as rhodium formate; and (6) separation of rhodium and cobalt catalyst mixtures by treatment of the catalyst solution with halogen to remove cobalt halide from the unchanged rhodium carbonyls which are then precipitated by thermal treatment under a hydrogen atmosphere. None of these procedures can satisfactorily recover mixed rhodium and cobalt from a low pressure system wherein the metals are in the form of the aforesaid ligandized complexes.

The present process recovers essentially all of the rhodium and cobalt in a very simple manner comprising treating a by-product purge stream or other convenient stream containing the catalyst with an oxygen containing gas, preferably air, as taught, for example, in U.S. Pat. No. 4,196,096, in the presence of at least trace amounts of oxo aldehyde, e.g., at least about one mole of aldehyde for each mole of Rh, Co and associated ligand such as triphenylphosphine, and then reacting the metal oxidation products with aqueous formic acid, both of which steps can be carried out essentially simultaneously in the same unit and preferably in a continuous manner. The molar ratio of $O_2$ to Rh may be varied widely depending, for example, on the desired speed of reactivation, concentration of ligand, temperature rise, and the like, and this oxidation may be performed prior to or essentially simultaneously with the reaction with the formic acid. The $O_2$/Rh molar ratio can vary from e.g., 1/1 to about 10,000/1, but preferably is between about 1,000/1 to about 4,500/1 for both the batch and continuous regenerations, with from about 2,500/1 to about 3,500/1 being most preferred. Typically the by-product stream contains rhodium, cobalt and ligand such as triphenylphosphine in a molar ratio of about 1/2/10 respectively, however, this ratio can range, for example, as Rh/Co of 5/1 to 1/50, and (Rh+Co)/ligand of 1/1 to 1/500 depending on the particular ratios of catalyst components and ligand fed to the hydroformylation reactor. The water soluble metal formates are readily separable from the organic phase containing, for example, high boiling by-products and oxidized ligand, e.g., triphenylphosphine oxide. The metal formates may be separated from each other in known manner if desired, and converted to and used as carbonyl complexes which may be designated as the unmodified species, in high pressure oxo processes, or may be recycled to the low-pressure reactor as is or with make-up ligand if needed, for the in-situ generation of the modified species. The oxo activity of the resulting catalyst is essentially that of the original catalyst feed.

The present invention is defined, therefore, as a process for recovering rhodium and cobalt from an oxo catalyst solution containing ligandized (modified) rhodium and cobalt, organic solvent, and at least trace amounts of oxo aldehyde, which comprises contacting said catalyst solution with an oxygen containing gas and aqueous formic acid to form an organic layer and an aqueous layer, said aqueous layer having rhodium and cobalt formate solubilized therein, and thereafter separating said layers.

In the present recovery process sufficient oxygen containing gas is used to deligandize the catalyst and convert all of the ligand including any excess thereof to its oxides which are retained in the organic layer. The ratio by volume of 100% formic acid to catalyst solution in both the batch and continuous recovery processes is from about 1/10 to 10/1, and preferably 1/2 to 4/1, these ratios being significant only from the standpoint of having sufficient formic acid present to maintain the rhodium as its salt. The volumetric ratio of water to $CH_2O_2$ in the feed can vary widely; e.g., between about 1000 to 1 to 1 to 100, preferably from 50/1 to 1/20, with between about 20/1 to 1/1 being most preferred. In the continuous and preferred recovery operation wherein there is a continuous feed of (1) aqueous formic acid, (2) catalyst solution, and (3) air, the volumetric feed ratio of (1)/(2) based on 100% formic acid can be, for example, from 1/10 to 10/1, and preferably 1/2 to 4/1. The recovery reaction temperatures may range between about 30° C. and about 90° C., and preferably from about 50° C. to about 70° C.

The aqueous solution of rhodium formate and cobalt formate may be recycled directly to the low pressure oxo reactor with or without additional solvent such as 2,2,4-trimethyl-1,3-pentanediol monoisobutyrate (TMPDMI), and ligand such as triphenylphosphine, whereupon the water and formic acid are stripped from the reactor leaving the catalyst in organic solution. The volume of water and excess formic acid introduced into the oxo reactor from the recovery unit is not critical but a minimum is preferred from the standpoint of efficiency.

Under the oxo conditions, the rhodium and cobalt formates are readily converted to the ligandized complexes in the reactor wherein an excess of ligand reactant is present. Alternatively, the formates can be ligandized readily by reacting them in known manner with e.g., triphenylphosphine at room temperature prior to recycling to the reactor. The types of ligands to which the present invention is applicable include trialkylphosphites, alkyldicycloalkylphosphines, tricycloalkylphosphites, tricycloalkylphosphines, triarylphosphites, dialkylcycloalkylphosphines, arylalkylphosphines, triarylphosphines, triarylstibines, trialkylphosphines, and triarylarsines. Preferably, each organo moiety in the ligand should not exceed 18 carbon atoms. Typical are trimethylphosphite, triethylphosphite, butyldiethylphosphite, tri-n-propylphosphite, tri-n-butylphosphite, tri-2-ethylhexylphosphite, tri-n-octylphosphite, tri-n-dodecylphosphite, triphenylphosphite, trinaphthylphosphite, triphenylphosphine, tri(p-chlorophenyl) phosphite, trinaphthylphosphine, tricyclohexylphosphine, phenyldiphenylphosphinite, diphenylphenylphosphonite, diphenylethylphosphonite, triphenylarsine, triphenylstibine, tris(p-chlorophenyl)phosphine, tri(p-cyanophenyl) phosphite, tri(p-methoxyphenyl)phosphite, ethyldiphenylphosphinite, and the like.

Typical solvents employed in oxo processes and to which the present invention is applicable are those selected from the following which are substantially immiscible with water: benzene, xylene, toluene and their substituted derivatives, pentanes, naphtha, kerosene, mineral oils, cyclohexane, cyclopentane, ethers, esters, etheresters, alcohols, acetals, ketones, and various mixtures thereof. Preferred solvents are those which are sufficiently high boiling to remain in the gas sparged reactor, and include 2,2,4-trimethyl-1,3-pentanediol monoisobutyrate (TMPDMI), and its isomers, and the by-products such as alcohols, esters, acetals, and hydroxyaldehydes produced in the hydroformylation reaction.

The following examples will further assist in understanding the present invention.

EXAMPLE 1

Preparation of n- and i-Butyraldehyde Using Fresh Rhodium Isobutyrate and Cobalt Isobutyrate in a Low Pressure Oxo Reactor A TMPDMI catalyst solution (175 ml) containing rhodium isobutyrate ($3.34 \times 10^{-4}$ moles), cobalt isobutyrate ($6.8 \times 10^{-4}$ moles), and triphenylphosphine ($3.35 \times 10^{-3}$ moles) having a molar ratio of Rh/2 Co/10 Ph$_3$P was charged to a low pressure oxo reactor pressured to 250 psig with H$_2$, CO and propylene in a molar ratio of 1:1:1, at 125° C. Product butyraldehydes were continuously gas stripped out of the reactor with concurrent addition of propylene and synthesis gas in the above ratio to the reactor to maintain approximately the aforesaid pressure. An average production rate of 36.6 pounds per cubic foot-hour was obtained during the 3.5-hour run time, and the ratio of n- to i-butyraldehyde was 1.5.

The above oxo run was repeated twice more using identical catalyst concentrations and reaction conditions. The catalyst solutions from the three runs were combined to provide the catalyst feed for the extraction experiments described below. It is noted that the volume of the catalyst solution at the end of each run increased over 175 ml due to the formation of high boilers.

Example 2 illustrates the inefficiency of the aqueous formic acid extraction of rhodium from an organic solution containing the triphenylphosphine modified rhodium and cobalt catalyst which has not been treated with air.

EXAMPLE 2

Aqueous Formic Acid Extraction of the Unoxidized Triphenylphosphine Modified Rhodium and Cobalt Carbonyl Catalyst A 200 ml portion of the TMPDMI catalyst solution of Example 1 was extracted five times with 200 ml portions of 20 percent aqueous formic acid by mixing the organic catalyst solution and aqueous formic acid and heating to 60° C. with vigorous agitation. After one hour, the mixture was cooled and the aqueous and organic layers separated. The combined aqueous extracts were found to contain 99 percent of the cobalt and only 0.8 percent of the rhodium.

EXAMPLE 3

Recovery of Rhodium and Cobalt by Air Oxidation of the Catalyst Solution Prior to Aqueous Formic Acid Extraction A 200 ml portion of the TMPDMI catalyst solution of Example 1 was air oxidized for 30 minutes at 55° C. and extracted five times with aqueous formic acid as in Example 2. The combined aqueous extracts contained 73 percent of the rhodium and 100 percent of the cobalt.

EXAMPLE 4

Recovery of the Mixed Metal Catalyst by the Concurrent Air Oxidation and Aqueous Formic Acid Treatment Method A 200 ml portion of the TMPDMI catalyst solution of Example 1 was mixed with 200 ml of 20 percent aqueous formic acid at 25° C. with air bubbling into the solution for about twenty minutes. The solution was then heated to 60° C. with vigorous stirring and maintained at 60° C. for one hour. The extraction procedure was repeated five times as in Example 2 and the combined aqueous extracts were found to contain 95 percent of the rhodium and 100 percent of the cobalt.

The recovery of rhodium and cobalt in the batchwise fashion described above is merely for the purpose of illustration and extremely efficient recovery of rhodium can be obtained using known continuous countercurrent extraction procedures exemplified below.

EXAMPLE 5

Preparation of n- and i-Butyraldehyde Using Recovered Rhodium Formate and Cobalt Formate in the Low Pressure Oxo Reactor A TMPDMI solution (175 ml) containing triphenylphosphine ($3.35 \times 10^{-3}$ moles) was combined with a sample of concentrated catalyst solution obtained from the extraction step of Example 4, containing rhodium formate ($3.2 \times 10^{-4}$ moles) and cobalt formate ($6.8 \times 10^{-4}$ moles) and charged to the oxo unit of Example 1. For comparison with Example 1 above, the low pressure run was conducted as in Example 1 and an average production rate of 36.2 pounds per cubic foot per hour of reactor volume was obtained during the 3.5 hour run time. The ratio of n- to i-butyraldehyde was 1.6.

EXAMPLE 6

Extraction of Previously Air Treated Catalyst Solution In Continuous Extractor

The raw catalyst solution (organic) used in this example was indentical in composition to that of Example 1.

The process parameters used in the continuous extraction are those which would approximate a plant scale process. The extractor was a York-Scheibel model, 3-inch inside diameter glass column with 14 stirred stages and measuring 130 cm from the bottom organic inlet to the top organic outlet. The organic/aqueous interface (aqueous formic acid inlet) was 2 inches below the top organic outlet for maximum contact of the organic phase with the aqueous phase; however, the position of the interface can be adjusted to regulate the residence time of the organic phase in the aqueous phase. The heavier aqueous phase moves down the column countercurrently to the rising lighter organic phase. The extractions were run at 60° C. for 12 hours. The following parameters were used in the extraction.

Organic Feed Rate—102 ml/hr
20 Percent Aqueous Formic Acid Feed Rate—985 ml/hr
Organic Residence Time—6.7 Minutes The 1,224 ml of organic solution was treated in a vented flask with 750 liters of air ($O_2$/Rh mole ratio of about 3,000/1) at 60° C. for 30 minutes prior to beginning the extraction experiment. The organic feed to the extractor contained a total of 214.2 mg. of rhodium and 244.8 mg of cobalt. The extraction retrieved 78% of the rhodium and 100% of the cobalt.

EXAMPLE 7

Concurrent Air Treatment and Continuous Extraction of Catalyst Solution

This example shows the unexpected advantages of continuously and concurrently air oxidizing and extracting the catalyst solution at 60° C. The organic and aqueous compositions and feed rates to the extractor were the same as in Example 6. Air was introduced into the bottom of the extractor of Example 6 at a rate of approximately 0.84 liters per minute. This extraction retrieved 97.6% of the rhodium and 100% of the cobalt.

The invention has been described in detail with particular reference to preferred embodiments thereof, but it will be understood that variations and modifications can be effected within the spirit and scope of the invention.

I claim:

1. A process for recovering rhodium and cobalt from an oxo catalyst solution containing ligandized (modified) rhodium and cobalt in a molar ratio of Rh/Co of 5/1 to 1/50, and a molar ratio of (Rh+Co)/Ligand of from about 1/1 to 1/500, organic solvent, and at least trace amounts of oxo aldehyde, which comprises contacting said catalyst solution with an oxygen containing gas in an $O_2$/Rh molar ratio from about 1/1 to about 10,000/1, and with sufficient aqueous formic acid to convert the rhodium and cobalt to stable formates and to form an organic phase and an aqueous phase, wherein the rhodium and cobalt formates are solubilized in said aqueous phase, and thereafter separating said phases.

2. The process of claim 1 wherein said catalyst solution is first contacted with said oxygen containing gas for a sufficient period to deligandize the rhodium and cobalt, and thereafter is contacted with said aqueous formic acid.

3. The process of claim 1 wherein said catalyst solution is contacted simultaneously with said oxygen containing gas and said aqueous formic acid.

4. The processes of claim 1 wherein said catalyst solution is contacted with said oxygen containing gas at a temperature from about 30° C. to about 90° C.

5. The process of claim 1 wherein the ratio by volume of 100% formic acid to catalyst solution is from about 1/10 to 10/1.

6. The process of claim 1 carried out in a continuous extractor with a continuous feed of (1) aqueous formic acid, (2) catalyst solution, and (3) air, wherein the volumetric feed ratio of (1)/(2) based on 100% formic acid is from 1/10 to 10/1, and the volumetric feed ratio of (2)/(3) is from 1/100 to 1/10,000.

7. The process of claim 6 wherein the volumetric feed ratio of (1)/(2) is from 1/2 to 4/1, and the volumetric feed ratio of (2)/(3) is from 1/1,000 to 1/4,500.

* * * * *